(12) United States Patent
Taber et al.

(10) Patent No.: US 11,839,537 B2
(45) Date of Patent: Dec. 12, 2023

(54) HYDRAULIC DELIVERY OF SURGICAL IMPLANTS

(71) Applicant: Alcon Inc., Fribourg (CH)

(72) Inventors: Todd Taber, Keller, TX (US); Kate Jensen, Sugar Land, TX (US); Jestwin Edwin Lee, IV, Grandview, TX (US); Pradeep Magadum, Arlington, TX (US); Saumya Dilip Yadav, Arlington, TX (US)

( * ) Notice: Subject to any disclaimer, the term of this patent is extended or adjusted under 35 U.S.C. 154(b) by 253 days.

(21) Appl. No.: 17/335,553

(22) Filed: Jun. 1, 2021

(65) Prior Publication Data

US 2022/0142767 A1 May 12, 2022

Related U.S. Application Data

(60) Provisional application No. 63/112,692, filed on Nov. 12, 2020.

(51) Int. Cl.
*A61F 2/16* (2006.01)
*A61F 2/48* (2006.01)

(52) U.S. Cl.
CPC ............ *A61F 2/167* (2013.01); *A61F 2/1675* (2013.01); *A61F 2/484* (2021.08)

(58) Field of Classification Search
CPC .... A61F 2/14; A61F 2/148; A61F 2/16; A61F 2/167; A61F 9/00; A61F 9/0008; A61F 9/0017; A61F 9/0026; A61F 9/0061; A61F 9/007; A61B 17/3468
See application file for complete search history.

(56) References Cited

U.S. PATENT DOCUMENTS

| | | | |
|---|---|---|---|
| 8,956,408 B2 | 2/2015 | Smiley | |
| 8,968,396 B2 | 3/2015 | Matthews et al. | |
| 9,610,155 B2 | 4/2017 | Matthews | |
| 9,693,858 B2 | 7/2017 | Hildebrand et al. | |
| 9,855,139 B2 * | 1/2018 | Matthews | ............ A61F 2/1678 |
| 10,195,020 B2 | 2/2019 | Matthews | |
| 2014/0276898 A1 | 9/2014 | Novak | |

FOREIGN PATENT DOCUMENTS

| | | |
|---|---|---|
| EP | 1800623 A1 | 6/2007 |
| EP | 3560457 A1 | 10/2019 |
| JP | 2010063777 A | 3/2010 |

* cited by examiner

*Primary Examiner* — Sarah W Aleman

(57) ABSTRACT

An apparatus for eye surgery may comprise a nozzle having a delivery lumen, an implant bay coupled to the nozzle, an implant disposed in the implant bay, and an actuator coupled to the implant bay. The actuator may comprise a housing, a plunger disposed within the housing, a bore through the plunger, a first coupling proximate to a first end of the plunger, and a second coupling integral to the housing. The bore may be fluidly coupled to the implant bay. The first coupling may be configured to receive a hydraulic driver and fluidly couple a working fluid in the hydraulic driver to the bore. A portion of the plunger may be slidingly disposed through the second coupling. In some embodiments, the second coupling may be configured to retain a drive coupling of the hydraulic driver in a fixed position relative to the housing.

14 Claims, 3 Drawing Sheets

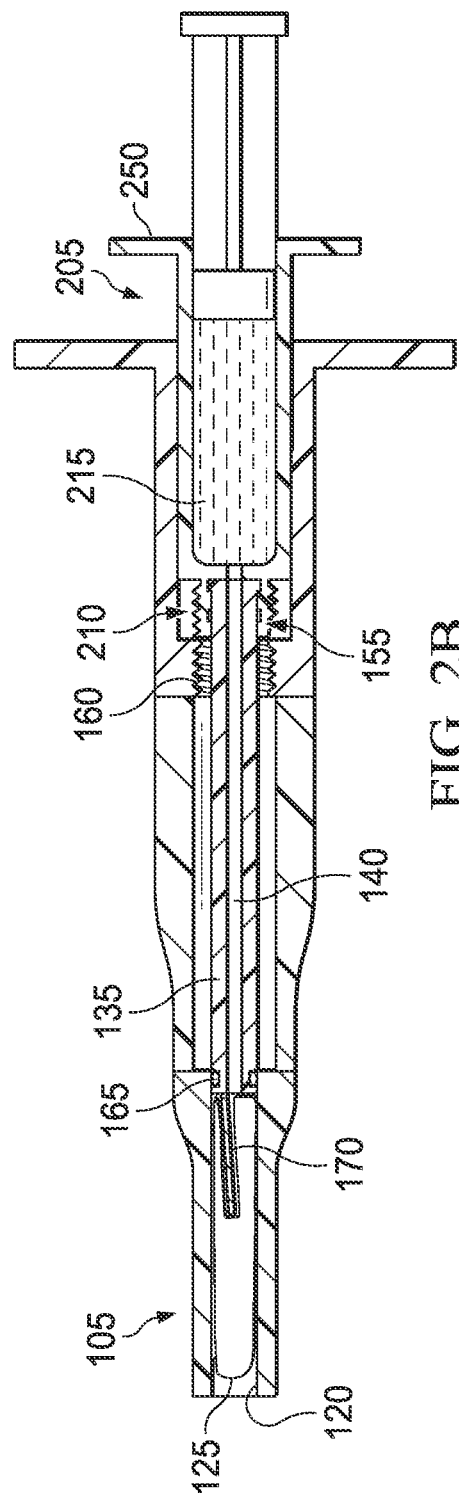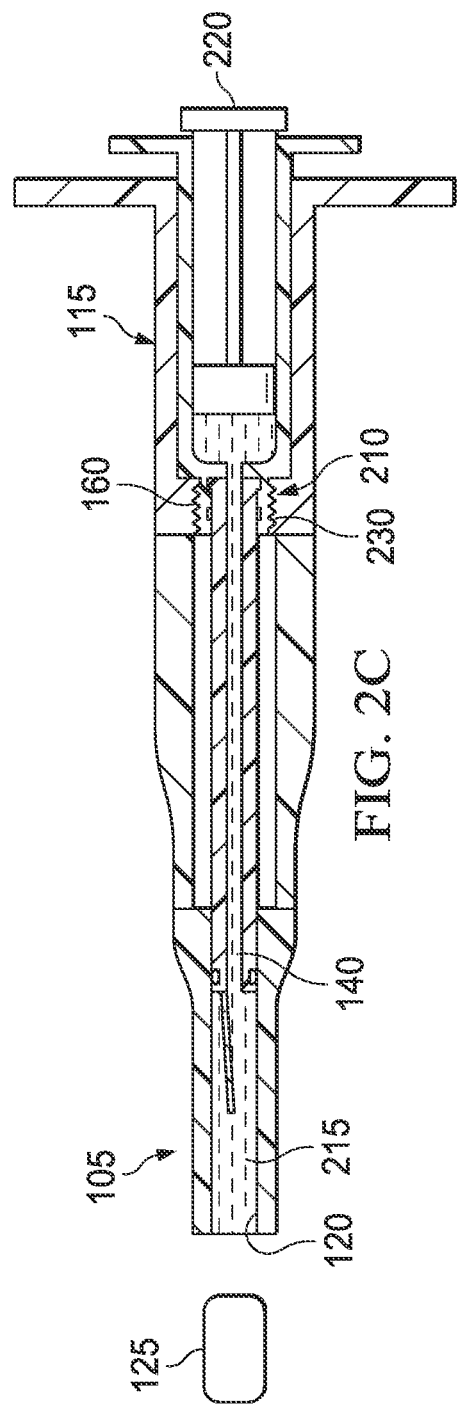

HYDRAULIC DELIVERY OF SURGICAL IMPLANTS

PRIORITY CLAIM

This application claims the benefit of priority of U.S. Provisional Patent Application Ser. No. 63/112,692 titled "HYDRAULIC DELIVERY OF SURGICAL IMPLANTS," filed on Nov. 12, 2020, whose inventor is Todd Taber, Kathryn Jensen, Jestwin Edwin Lee, IV, Pradeep Magadum, Saumya Dilip Yadav, which is hereby incorporated by reference in its entirety as though fully and completely set forth herein.

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments may comprise or consist essentially of an apparatus for delivering an implant, such as an intraocular lens, using hydraulic pressure or fluid flow. The apparatus may be combined with a disposable hydraulic driver, such as a vial of working fluid, to provide a fully disposable system for storing, advancing, and delivering an implant. In more particular examples, the apparatus may comprise a rigid plunger for advancing an implant to a sealed position in a first phase, and a bore through the rigid plunger that allows a working fluid to advance the implant into the eye via hydraulic pressure in a second phase. For example, a hollow rigid plunger can be used to first advance an intraocular lens in a straight-straight configuration to a point that a seal is created about the intraocular lens within a delivery lumen. The lens may then be hydraulically advanced to delivery by passing a working fluid through the hollow bore of the plunger. In some embodiments, the tip of the plunger may have an implant interface. For example, the tip may have a notch for engaging a shoulder of the optic body of the lens and advancing the lens into the delivery lumen. The apparatus may additionally comprise a plunger stop, which may be configured to stop advancement of the implant interface or the plunger.

In other more particular embodiments, a vial of working fluid may be used as a hydraulic driver for advancing and delivering an intraocular lens in a delivery system. For example, the vial may connect via a luer lock to the back of a plunger in the delivery system. The delivery system can straighten one or more haptics of the lens, such as the leading haptic and prepare the lens for advancement. The vial may be advanced forward, thereby advancing the plunger and the lens to a second position where an end of the vial engages a coupling in the delivery system. The coupling can prevent removal of the vial. For example, the vial may have external threads, and the coupling may have internal threads configured to receive the external threads of the vial. The vial may have a second plunger, which can be pressed to move the working fluid out of the vial and through a bore in the plunger of the delivery system to eject the lens from the delivery system.

More generally, an apparatus for advancing an implant in an implant delivery system may comprise a housing, a plunger disposed within the housing, a bore passing through the plunger from a first end to a second end, a first coupling proximate to the first end, and a second coupling integral to the housing. The bore may be configured to be fluidly coupled to the implant bay. The first coupling can be configured to receive a hydraulic driver and fluidly couple a working fluid in the hydraulic driver to the bore. A portion of the plunger may be slidingly disposed through the second coupling, and the second end of the plunger may be configured to engage the implant. In some embodiments, the second coupling may be configured to retain a drive coupling of the hydraulic driver in a fixed position relative to the housing. In more particular embodiments, the second coupling may comprise or consist essentially of a thread trap configured to engage the drive coupling.

In other embodiments, an apparatus for eye surgery may comprise a nozzle having a delivery lumen, an implant bay coupled to the nozzle, an implant disposed in the implant bay, and an actuator coupled to the implant bay. The actuator may comprise a housing, a plunger disposed within the housing, a bore through the plunger, a first coupling proximate to a first end of the plunger, and a second coupling integral to the housing. The bore may be fluidly coupled to the implant bay. The first coupling may be configured to receive a hydraulic driver and fluidly couple a working fluid in the hydraulic driver to the bore. A portion of the plunger may be slidingly disposed through the second coupling. In some embodiments, the second coupling may be configured to retain a drive coupling of the hydraulic driver in a fixed position relative to the housing. In more particular embodiments, the second coupling may comprise or consist essentially of a thread trap configured to engage the drive coupling.

A method of ejecting an implant from an implant delivery system may comprise providing the implant in an implant bay. In some examples, the implant may be a lens, such as an intraocular lens. A hydraulic driver may be coupled to a rigid plunger of the implant delivery system, and the hydraulic driver may drive the rigid plunger to advance the implant from the implant bay to a delivery lumen in the implant delivery system. The hydraulic driver may be retained in a fixed position relative to the implant delivery system. A working fluid in the hydraulic driver may be pressed to move the working fluid through a bore in the rigid plunger to the delivery lumen, and the working fluid may advance the implant through the delivery lumen.

Such embodiments may be particularly advantageous for delivering intraocular lenses, including accommodating lenses, which can present unique challenges for delivery. Some embodiments can manage fluid in the accommodating lens to compress a relatively large lens for advancement through an acceptably small incision, manage deformation caused by shifting fluid during compression and exit from a nozzle, and execute delivery in a predictable and controlled manner. An intraocular lens may additionally include one or more haptics, which can extend radially to secure the lens within an eye. Some embodiments can reduce system complexity and the number of delivery steps while maintaining haptic position consistency. Some embodiments may also reduce the amount of working fluid for delivery.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

FIGS. 2A-2C are schematic diagrams illustrating the operation of the example system of FIG. 1.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
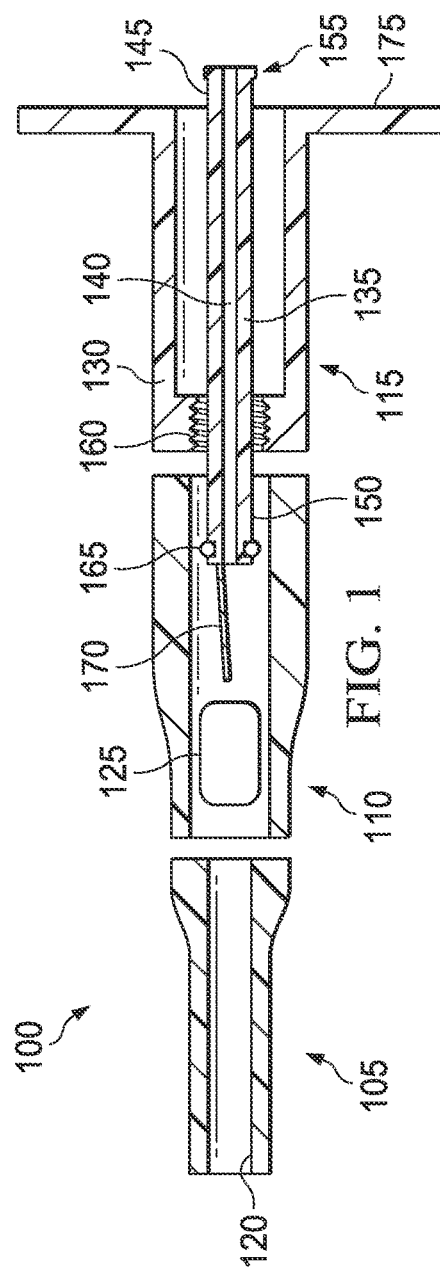
FIG. 1 is a schematic diagram of an example system for inserting an implant into an eye.

FIG. 1 is a schematic diagram of a system 100 that can be used to deliver an implant into an eye. For example, as illustrated in FIG. 1, some embodiments of the system 100 may include a nozzle 105, an implant bay 110 that can be coupled to the nozzle 105, and an actuator 115 that can be coupled to the implant bay 110.

In general, components of the system 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, the actuator 115 may be mechanically and fluidly coupled to the nozzle 105. In some embodiments, components may also be coupled by virtue of physical proximity, being integral to a single structure, or being formed from the same piece of material.

The nozzle 105 generally comprises a tip adapted for insertion through an incision into an eye. The size of the tip may be adapted to surgical requirements and techniques as needed. For example, small incisions are generally preferable to reduce or minimize healing times. Incisions of less than 3 millimeters may be preferable in some instances, and the tip of the nozzle 105 may have a width of less than 3 millimeters in some embodiments. The nozzle 105 of FIG. 1 has a delivery lumen 120.

The implant bay 110 generally represents a wide variety of apparatuses that are suitable for storing an implant prior to delivery into an eye. In FIG. 1, for example, an implant 125 is disposed within the implant bay 110.

The actuator 115 of FIG. 1 generally comprises a housing 130, a plunger 135 disposed within the housing 130, and a bore 140 through the plunger 135. The plunger 135 is generally comprised of a substantially rigid material, such as a medical grade polymer material. The bore 140 generally passes through the plunger 135 longitudinally from a first end 145 to a second end 150. The actuator 115 may additionally comprise a first coupling 155 proximate to the first end 145 of the plunger 135. A second coupling 160 may be integral to the housing 130, and a portion of the plunger 135 may be slidingly disposed through the second coupling 160.

In some embodiments, the actuator 115 may additionally comprise a nozzle seal 165. As illustrated in the example of FIG. 1, the nozzle seal 165 may be a ring seal, such as an O-ring, disposed circumferentially around a portion of the plunger 135. In other examples, an umbrella seal may be suitable. In more particular embodiments, the nozzle seal 165 may be disposed proximate to the second end 150 of the plunger 135.

Some embodiments of the actuator 115 may also comprise an implant interface 170. For example, in some embodiments, the implant interface 170 of FIG. 1 may be coupled to the second end 150 of the plunger 135.

Some embodiments of the system 100 may additionally include various ergonomic features. For example, the system 100 of FIG. 1 has a finger flange 175 coupled to the actuator 115, which can facilitate one-handed manipulation of the system 100.

Figure 2A:
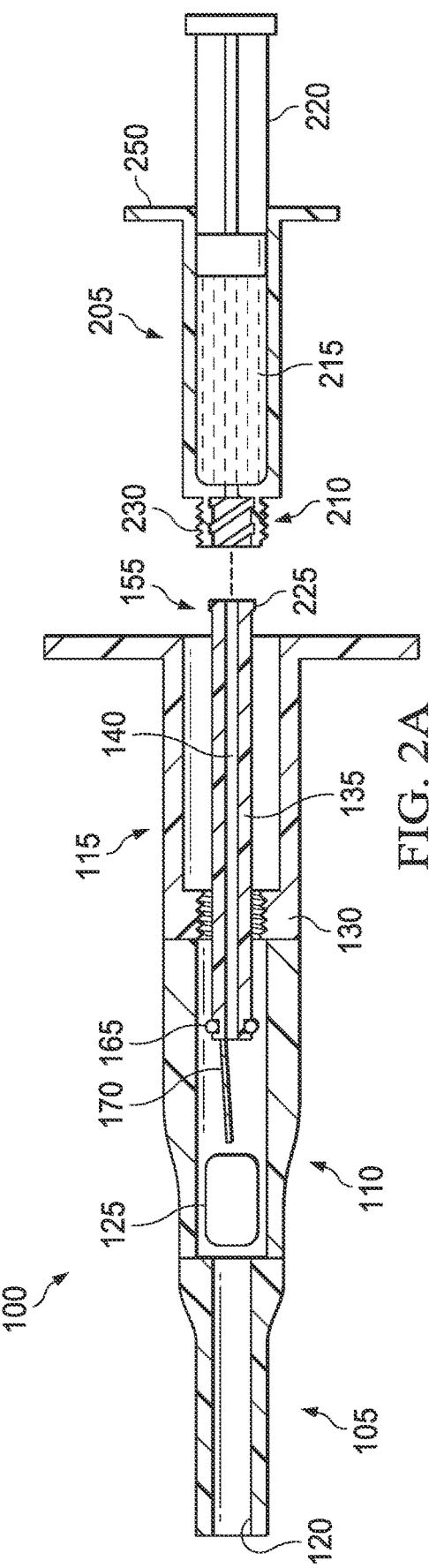

FIGS. 2A-2C are schematic diagrams illustrating the operation of the system 100 of FIG. 1. Initially, various components of the system 100 may be assembled if needed. In the example of FIGS. 2A-2C, the nozzle 105, the implant bay 110, and the actuator 115 are fixed together to form a unitary structure. In other embodiments, the system 100 may comprise two or more modules, which can be configured to be coupled and decoupled as appropriate for storage, assembly, use, and disposal.

If assembled as illustrated in FIG. 2A, the implant bay 110 may be disposed between the bore 140 and the delivery lumen 120. A portion of the plunger 135 and the implant interface 170 may extend into the implant bay 110, and the implant interface 170 may be configured to engage the implant 125.

In the example of FIG. 2A, the system 100 is configured to receive a hydraulic driver 205. The hydraulic driver 205 of FIG. 2A generally comprises a drive coupling 210, a working fluid 215, and a drive plunger 220. In some embodiments, the hydraulic driver 205 may comprise or consist essentially of a vial of working fluid. Suitable working fluids may include, without limitation, a liquid, such as saline, or a viscous lubricant with non-Newtonian properties.

The first coupling 155 of the actuator 115 may be configured to receive the hydraulic driver 205 and to fluidly couple the working fluid 215 in the hydraulic driver 205 to the bore 140. For example, the drive coupling 210 may be configured to be coupled to the first coupling 155 of the actuator 115. In some embodiments, the first coupling 155 may be a luer lock, luer slip, or similar fitting configured to receive the drive coupling 210. For example, the first coupling 155 may comprise a male luer lock having at least one locking tab 225, and the drive coupling 210 may comprise a female luer lock configured to receive the locking tab 225 of the first coupling 155. The drive coupling 210 may additionally comprise external threads 230.

The implant 125 may be provided in the implant bay 110, as illustrated in the example of FIG. 2A. In some embodiments, the implant 125 may comprise an intraocular lens having a shape similar to that of a natural lens of an eye, and it may be made from numerous materials. Examples of suitable materials may include silicone, acrylic, and combinations of such suitable materials. In some instances, the implant 125 may comprise an intraocular lens that is fluid-filled, such as a fluid-filled accommodating intraocular lens. The implant 125 may also comprise an intraocular lens that includes one or more features, such as haptics, for positioning the intraocular lens within an eye.

In some embodiments, the implant bay 110 may additionally or alternatively be configured to prepare the implant 125 for delivery. For example, some embodiments of the implant bay 110 may be configured to be actuated by a surgeon or other operator to prepare the implant 125 for delivery by subsequent action of the actuator 115. In some instances, the implant bay 110 may be configured to actively deform, elongate, extend, or otherwise manipulate features of the implant 125 before the implant 125 is advanced into the nozzle 105. For example, some embodiments of the implant bay 110 may be configured to orient or fold an implant. For example, the implant 125 may comprise one or more haptics, which can be oriented for delivery.

The plunger 135 is generally configured to advance the implant 125 from the implant bay 110 into the delivery lumen 120 of the nozzle 105. For example, if the drive coupling 210 is coupled to the first coupling 155, force can be applied to the hydraulic driver 205 to move the hydraulic driver 205 and the plunger 135 within the housing 130 from a first configuration illustrated in the example of FIG. 2A to a second configuration, as illustrated in the example of FIG. 2B. In the embodiment of FIG. 2A, for example, the hydraulic driver 205 comprises a flange 250, and pressure can be applied to the flange 250 to rigidly move the hydraulic driver 205 and the plunger 135 to the second configuration while maintaining the relative position of the drive plunger 220 and the working fluid 215. As illustrated in the example of FIG. 2B, the implant 125 may also be advanced into the delivery lumen 120 of the nozzle 105 by the implant interface 170. In the second configuration, the nozzle seal 165 is also advanced into the delivery lumen 120 to create a seal in the delivery lumen 120 behind the implant 125. The implant 125 may also form a seal with the delivery lumen 120 in some instances. In the configuration of FIG. 2B, the bore 140 may fluidly couple the working fluid 215 in the hydraulic driver 205 to the delivery lumen 120.

The drive coupling 210 may engage the second coupling 160 of the actuator 115 to retain the drive coupling 210 in a fixed position relative to the housing 130. For example, as illustrated in FIG. 2C, the drive coupling 210 may be inserted into the second coupling 160 to retain the drive coupling 210 against further force applied to the hydraulic driver 205. In some embodiments, the second coupling 160 may comprise a thread trap configured to engage the threads 230 of the drive coupling 210 to prevent further linear movement of the drive coupling 210. A suitable thread trap may comprise internal threads, teeth, or ratchet system configured to allow one-way insertion of the threads 230 into the second coupling 160, preventing further linear movement of the drive coupling 210 once inserted into the second coupling 160.

With the drive coupling 210 retained, the drive plunger 220 may be advanced to a third configuration, as illustrated in FIG. 2C, forcing the working fluid 215 through the bore 140 into the delivery lumen 120 behind the implant 125. Movement of the working fluid 215 from the bore 140 into the delivery lumen 120 under pressure from the drive plunger 220 can increase the pressure and flow rate of the working fluid 215 in the delivery lumen 120 behind the implant 125, which can advance the implant 125 further through the delivery lumen 120 until the implant 125 is ejected from the nozzle 105.

Figure 3A:
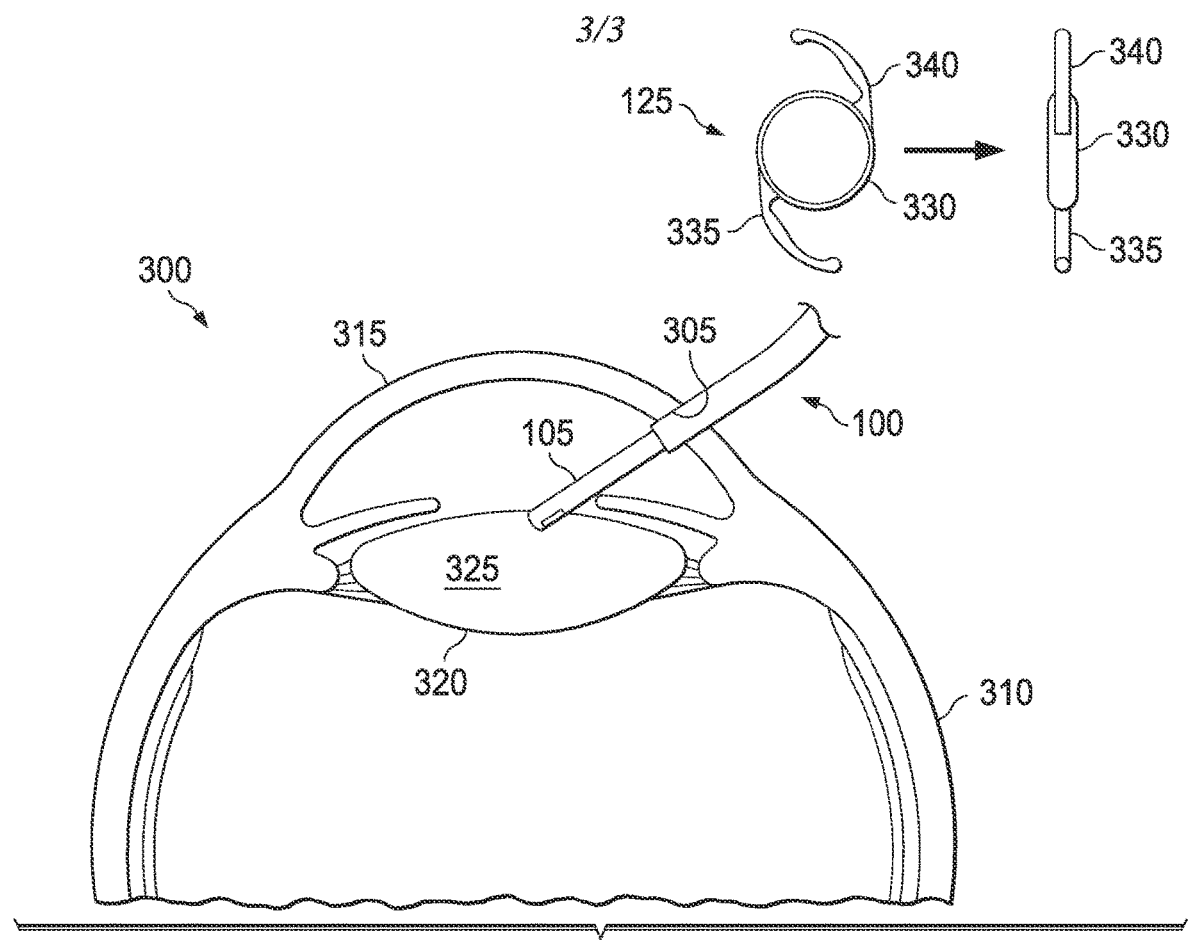
FIGS. 3A-3B are schematic diagrams illustrating an example application of the system of FIG. 1 to insert an implant into an eye.
Figure 3B:
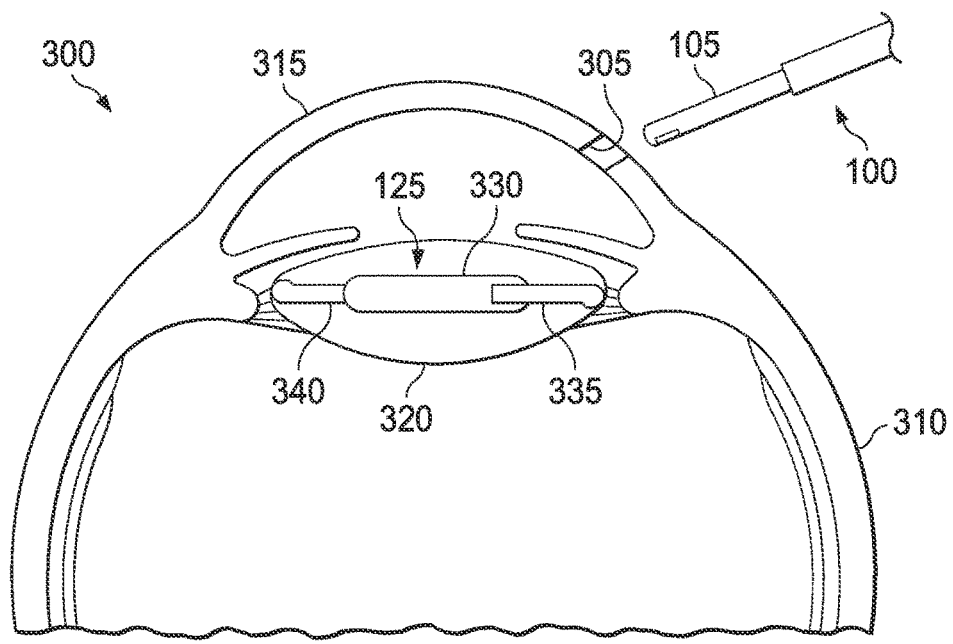

FIGS. 3A-3B are schematic diagrams further illustrating an example use of the system 100 to deliver the implant 125 to an eye 300. As illustrated, an incision 305 may be made in the eye 300 by a surgeon, for example. In some instances, the incision 305 may be made through the sclera 310 of the eye 300. In other instances, an incision may be formed in the cornea 315 of the eye 300. The incision 305 may be sized to permit insertion of a portion of the nozzle 105 to deliver the implant 125 into the capsular bag 320. For example, in some instances, the size of the incision 305 may have a length less than about 3000 microns (3 millimeters). In other instances, the incision 305 may have a length of from about 1000 microns to about 1500 microns, from about 1500 microns to about 2000 microns, from about 2000 microns to about 2500 microns, or from about 2500 microns to about 3000 microns.

After the incision 305 is made, the nozzle 105 can be inserted through the incision 305 into an interior portion 325 of the eye 300. The system 100 can then eject the implant 125 through the nozzle 105 into the capsular bag 320 of the eye 300, substantially as described above with reference to FIGS. 2A-2C. In some applications, the implant 125 may be delivered in a folded configuration and can revert to an initial, unfolded state, within the capsular bag 320, as shown in FIG. 3B. In the example of FIG. 3A and FIG. 3B, the implant 125 is illustrative of an intraocular lens having an optic body 330, a leading haptic 335, and a trailing haptic 340. For example, the implant 125 may be in the form of an accommodating intraocular lens having one or more of the optic body 330, the leading haptic 335, and the trailing haptic 340 filled with fluid. The capsular bag 320 can retain the implant 125 within the eye 300 in a relationship relative to the eye 300 so that the optic body 330 refracts light directed to the retina (not shown). The leading haptic 335 and the trailing haptic 340 can engage the capsular bag 320 to secure the implant 125 therein. After dispensing the implant 125 into the capsular bag 320, the nozzle 105 may be removed from the eye 300 through the incision 305, and the eye 300 can be allowed to heal over a period of time.

The systems, apparatuses, and methods described herein may provide significant advantages. For example, some embodiments may be particularly advantageous for delivering intraocular lenses, including fluid-filled accommodating lenses, which can present unique challenges for delivery. Some embodiments can compress a relatively large lens to fit through an acceptably small incision, manage deformation caused by shifting fluid during compression and exit from a nozzle, and execute delivery in a predictable and controlled manner. Additionally, some embodiments can reduce system complexity and the number of delivery steps while maintaining haptic position consistency. Some embodiments may also reduce the amount of working fluid for delivery. For example, a single vial of ophthalmic viscosurgical device (OVD), such as vial of CELLUGEL OVD, may be used to drive some embodiments of the system 100 and provide the working fluid for delivery.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations, the nozzle 105, the implant bay 110, and the actuator 115 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for eye surgery, the apparatus comprising:
   a nozzle having a delivery lumen;
   an implant bay coupled to the nozzle;
   an implant disposed in the implant bay; and
   an actuator coupled to the implant bay, the actuator comprising:
     a housing,
     a plunger disposed within the housing, the plunger having a first end and a second end,
     a bore through the plunger,
     a first coupling proximate to the first end, and
     a second coupling integral to the housing;
   wherein the bore is fluidly coupled to the implant bay, the first coupling is configured to receive a hydraulic driver and fluidly couple a working fluid in the hydraulic driver to the bore, and a portion of the plunger is slidingly disposed through the second coupling,
   wherein the second coupling is configured to retain a drive coupling of the hydraulic driver in a fixed position relative to the housing; and
   wherein the second coupling comprises a thread trap configured to engage the drive coupling.

2. The apparatus of claim 1, wherein the thread trap comprises internal threads configured to receive external threads on the drive coupling.

3. The apparatus of claim 1, wherein the thread trap comprises teeth.

4. The apparatus of claim 1, wherein the thread trap comprises a ratchet system.

5. The apparatus of claim 1, further comprising a nozzle seal disposed proximate to the second end of the plunger.

6. The apparatus of claim 1, further comprising an implant interface coupled to the second end of the plunger and configured to engage the implant.

7. The apparatus of claim 6, wherein the implant interface extends into the implant bay.

8. An apparatus for advancing a lens in an implant delivery system, the apparatus comprising:
   a housing configured to be coupled to an implant bay;
   a plunger disposed within the housing, the plunger having a first end and a second end;
   a bore passing through the plunger longitudinally from the first end to the second end;
   a first coupling proximate to the first end; and
   a second coupling integral to the housing;
   wherein the bore is configured to be fluidly coupled to the implant bay, the first coupling is configured to receive a hydraulic driver and fluidly couple a working fluid in the hydraulic driver to the bore, a portion of the plunger is slidingly disposed through the second coupling, and the second end of the plunger is configured to engage the lensi wherein the second coupling is configured to retain a drive coupling of the hydraulic driver in a fixed position relative to the housing; and
   wherein the second coupling comprises a thread trap configured to engage the drive coupling.

9. The apparatus of claim 8, wherein the thread trap comprises internal threads configured to receive external threads on the drive coupling.

10. The apparatus of claim 8, wherein the thread trap comprises teeth.

11. The apparatus of claim 8, wherein the thread trap comprises a ratchet system.

12. The apparatus of claim 8, further comprising a nozzle seal disposed proximate to the second end of the plunger.

13. The apparatus of claim 8, further comprising an implant interface coupled to the second end of the plunger and configured to engage the lens.

14. The apparatus of claim 13, wherein the implant interface is configured to extend into the implant bay.

* * * * *